United States Patent [19]
Langer et al.

[11] Patent Number: 6,080,890
[45] Date of Patent: Jun. 27, 2000

[54] PRODUCTION OF AROMATIC AMINES BY MEANS OF NOVEL HYDROGENATION CATALYSTS

[75] Inventors: Reinhard Langer, Tönisvorst; Hans-Josef Buysch, Krefeld; Manfred Gallus, Krefeld; Joerg-Dietrich Jentsch, Krefeld, all of Germany

[73] Assignee: Bayer Aktiengesellschaft, Leverkusen, Germany

[21] Appl. No.: 09/402,677

[22] PCT Filed: Apr. 6, 1998

[86] PCT No.: PCT/EP98/01985

§ 371 Date: Oct. 7, 1999

§ 102(e) Date: Oct. 7, 1999

[87] PCT Pub. No.: WO98/46557

PCT Pub. Date: Oct. 22, 1998

[30] Foreign Application Priority Data

Apr. 16, 1997 [DE] Germany .......................... 197 15 746

[51] Int. Cl.$^7$ .................................................. C07C 209/00
[52] U.S. Cl. ........................... 564/421; 564/423; 502/308
[58] Field of Search ............................ 502/308; 564/421, 564/423

[56] References Cited

U.S. PATENT DOCUMENTS

| | | | |
|---|---|---|---|
| 3,882,048 | 5/1975 | Thelen et al. | 252/464 |
| 3,960,964 | 6/1976 | Suggitt et al. | 260/583 |
| 4,265,834 | 5/1981 | Birkenstock et al. | 564/421 |
| 5,679,858 | 10/1997 | Langer et al. | 564/423 |

*Primary Examiner*—Samuel Barts
*Attorney, Agent, or Firm*—Joseph C. Gil; Lyndanne M. Whalen

[57] ABSTRACT

Aromatic amines are produced by catalytic hydrogenation of corresponding aromatic nitro compounds in the gas phase, by carrying out the hydrogenation in the presence of catalysts which, besides palladium, vanadium and lead, contain in addition molybdenum, tungsten and/or rhenium on a ceramic support having a BET surface area of less than 40 m$^3$/g, at temperatures of from 180° C. to 500° C. in a catalyst bed and in a molar ratio of hydrogen to the nitro group or nitro groups of 3:1 to 30:1.

2 Claims, No Drawings

PRODUCTION OF AROMATIC AMINES BY MEANS OF NOVEL HYDROGENATION CATALYSTS

This application is a 371 of PCT/EP98/01985 filed Apr. 6, 1998.

the present invention relates to the production of aromatic amines by catalytic hydrogenation of corresponding aromatic nitro compounds in the gas phase by means of new palladium-containing supported catalysts.

The hydrogenation of nitrobenzene to the corresponding aromatic amines in the gas phase on fixed palladium catalysts on ceramic supports is known. Thus a process for the reduction of nitro compounds in the presence of palladium-containing multicomponent supported catalysts in cooled tubular reactors is described in DE-A 2 849 002. The contact consists substantially of 1 to 20 g palladium, 1 to 20 g vanadium and 1 to 20 g lead per liter of $\alpha$-$Al_2O_3$. A disadvantage of the gas phase hydrogenations described in the cited patent publication is the low loading (specific loading) of the catalysts. The loadings given are approximately 0.4 to 0.5 kg/l×h. Here the loadings is defined as the quantity of nitroaromatics in kg which is reacted per liter of catalyst bed within one hour. Associated with the low catalyst loading is an unsatisfactory space-time yield in large-scale processes for the production of aromatic amines. Furthermore, the selectivities at the beginning of an operating period are significantly lower than the are towards the end, which results in losses in yield and problems in working up the crude product.

It was the object of the present invention to provide a process for the production of aromatic amines by catalytic hydrogenation of corresponding aromatic nitro compounds, which can be carried out on a large scale without problems, which renders possible a high space-time yield and which has a selectivity with regard to the required amines of $\geq 90\%$ even at the beginning of an operating period.

The present invention accordingly provides a process for the production of aromatic amines by catalytic hydrogenation of corresponding aromatic nitro compounds in the gas phase, which is characterised in that the hydrogenation is carried out in the presence of catalysts which, besides palladium, vandium and lead, contain in addition molybdenum, tungsten and/or rhenium on a ceramic support material having a BET surface area of less than 40 m³/g, at temperatures of from 180° C. to 500° C. in a catalyst bed and in a molar ratio of hydrogen to the nitro group or nitro groups of from 3:1 to 30:1.

Aromatic nitro compounds which can be hydrogenated by the process according to the invention are in particular those corresponding to the following formula:

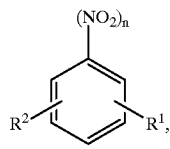

wherein
R¹ and R² are identical or different and represent hydrogen or $C_1$–$C_4$-alkyl, in particular methyl and ethyl, and n denotes 1 or 2.

Preferably nitrobenzene or the isomeric nitrotoluenes are hydrogenated by the process according to the invention.

Suitable ceramic support materials for the catalysts according to the invention include in principle all ceramic solids having BET surface areas of less than 40 m²/g, preferably of less than 20 m²/g, in particular of less than 10 m²/g. The following compounds in particular are suitable as ceramic solids: metal oxides and/or mixed metal oxides of the elements magnesium, aluminium, silicon, germanium, zirconium and titanium: $\alpha$-aluminium oxide is preferably used as support material.

Surprisingly, it has been found that contacts which, besides palladium, vanadium and lead, also contain Mo, W and/or Re deposited in the form of a shell on the above-mentioned support materials, in particular $\alpha$-aluminium oxide, are particularly stable, highly loadable and selective catalysts. Special emphasis is therefore placed on catalysts which contain a) from 1 to 50 g palladium, b) from 1 to 50 g vanadium, c) from 1 to 20 g lead and d) from 1 to 20 g molybdenum, tungsten and/or rhenium per liter of oxide support material, the support material having a surface area of less than 40 m²/g, preferably of less than 20 m²/g and in particular of less than 10 m²/g. Catalysts which contain 10 to 50 g Pd, 10 to 50 g V, 8 to 16 g Pb and 8 to 16 g Re on $\alpha$-$Al_2O_3$ are particularly preferably used.

The preparation of precious metal supported catalysts is known in principle. Here it has proved to be advantageous when the active components of the catalyst are deposited as a distinct zone as close as possible to the surface of the support body and when the interior of the support material does not contain any metal. The catalysts may be prepared with or without pretreatment of the support material with a base. It is preferable to pre-impregnate the support material with an alkali metal hydroxide solution or an alkaline-earth hydroxide solution before the impregnations.

The metals may be applied to the support individually or as a mixture in the form of solutions of their salts. Suitable salts are, for example, the halides, acetates, carbonates, hydrogen carbonates, sulphates, phosphates, oxalates, formates, oxides and hydroxides. After each impregnation and/or at the end of the process a reduction is carried out, for which hydrogen, hydrazine and/or formic acid is used.

The supported catalysts according to the invention may in principle be of any shape, such as balls, rods, raschig rings, granules or pellets. It is preferable to use mouldings which form beds having, a low resistance to fluid flow together with a good gas-surface contact, such as raschig rings, saddles, cartwheels and/or spirals. The catalysts according to the invention may be used pure or diluted with other inert filling materials, for example, made of glass, ceramic or metal. The catalyst bed may consist of up to 90 wt. %, preferably up to 75 wt. %, in particular up to 50 wt. %, of inert filling material or support material. In this connection the bed may have a dilution gradient such that the dilution decreases in the direction of flow. The bed may contain between 50 and 90 wt. % filling material at the upstream surface and may consist of between 80 and 100 wt. % of pure supported catalyst at the discharge end.

In the process according to the invention, the supported catalysts are used in quantities of from 40 to 80% and preferably in quantities of from 50 to 70%, based on the total volume of the bed.

The molar ratio of hydrogen to nitro compounds (nitro groups) used in the process according to the invention is 4:1 to 20:1, in particular 5:1 to 10:1. Here the hydrogen concentration may be decreased by admixing inert gases, such as nitrogen, helium, argon and/or water vapour. The admixed inert gas is preferably nitrogen. Up to 10 mol, preferably up to 3 mol and in particular up to 1 mol, inert gas may be admixed per mol of hydrogen.

The dilution with an inert carrier gas is carried out preferably at the beginning of an operating period using fresh catalyst and following the regeneration of the catalyst by burning off with air and reduction with hydrogen. Dilution with inert gas is carried out preferably in the first 300 hours, particularly preferably in the first 200 hours, in particular in the first 100 hours after restarting.

The regeneration of deactivated catalyst beds is carried out using nitrogen/oxygen mixtures at temperatures of from 200° C. to 400° C. preferably from 250° C. to 350° C., on the actual catalyst. The process is begun with $N_2$ contents of from 90 to 99% in the gas flow and during the burning-off the $O_2$ content is gradually increased to that of pure air. At the end of the regeneration persistent carbonisations can if necessary be burned off with pure oxygen. Instead of nitrogen, other inert carrier gases, such as argon, helium and/or water vapour, may also be admixed to oxygen or air. The process according to the invention is carried out at temperatures preferably of from 200° C. to 460° C. in particular at 220° C. to 440° C. Here it may be advantageous if the temperature of the cooling medium in the process according to the invention is continuously or gradually increased during an operating cycle.

The $H_2$ pressure in the process according to the invention is from 0.5 to 5 bar, preferably from 1 to 3 bar.

The loadings of the catalysts according to the invention with aromatic nitro compound introduced should be increased, continuously or stepwise, from 0.01 up 0.2 to 0.5 up to 5.0 kg/l, the maximum loading being attained within 10 to 1,000 hours.

For the catalysts according to the invention it is particularly beneficial that the loading with aromatic nitro compounds introduced be increased continuously or stepwise to the required loading within a certain period of time. A preferred procedure is therefore one wherein the loading of the catalyst is increased continuously or stepwise within the first 500 hours, in particular within the first 300 hours, most preferably within the first 200 hours, from 0.01 up to 0.5, preferably 0.1 up to 0.4, in particular 0.15 up to 0.3 to 0.6 up to 5.0, in particular from 0.6 up to 3.0, most preferably 0.6 up to 2.0 kg/l×h.

The high final loading is maintained constant until the emergence of the unreacted educt. If the level of the educt concentration at the end of the reactor is too high, the temperature of the heating medium can be raised and/or the loading with educt can be lowered in order to delay an interruption in production for regeneration of the catalyst.

A process using the catalysts according to the invention may be carried out industrially, for example, in the following way. A circulating flow of gas consisting substantially of hydrogen and a little water is compressed in order to overcome the resistance to fluid flow in the plant. The gas flow is heated by means of countercurrent heat exchange, the heat being removed, for example, from the circulating gas flow before the condensation of the products. The circulating gas flow is brought to the required temperature. In the fresh hydrogen, which replaces the spent hydrogen, the nitroaromatic to be hydrogenated is vaporised and superheated and then the two gas flows are mixed together. The gas mixture is passed into a thermostatted reactor containing a fixed-bed catalyst. The liberated heat of reaction is removed from the reactor by means of a heat-transfer medium. The product flow leaving the reactor is utilised for heating the circulating gas flow and is then cooled to a temperature at which the aniline and water formed are condensed. The liquids are transferred out, as well as a small quantity of circulating gas in order to remove gases, for example, nitrogen, which would otherwise accumulate. The circulating gas is subsequently returned to the compressor.

In a preferred embodiment, the catalyst according to the invention in the form of a bed is introduced into a reactor of the Linde type (heat-transfer medium flows inside the tubes of the reactor and the catalyst is arranged outside the tubes carrying the heat-transfer medium) and the procedure is carried out as described above. During the initial hours fresh or freshly-regenerated catalyst is activated with nitrogen-hydrogen mixtures. The advantages of this preferred mode of operation are high selectivities and long periods of time between the regenerations even after many production cycles.

The reactors used for the process according to the invention may be any of the known reactors which are suitable for gas phase reactions using cooled fixed catalyst beds. Suitable reactors include, for example, multitube reactors, wherein the catalyst is located inside tubes surrounded by a heat-transfer medium, and reactors wherein conversely the heat-transfer medium flows inside the tubes and the catalyst is located outside the tubes. Such reactors are known, for example, from DE-A 2 848 014 and 3 007 202.

Reactors wherein the heat-transfer medium flows inside the tubes and the catalyst is located outside the tubes carrying the heat-transfer medium (reactors of the Linde type) have proved to be particularly advantageous for the process according to the invention. In these reactors, compared with conventional multitube reactors, constant running times between the regenerations are observed over many regeneration cycles.

The length of the catalyst bed in the direction of flow is 0.5 to 20 m, preferably 1 to 10 m and particularly preferably 2 to 6 m in the process according to the invention.

The length of the bed may optionally also be achieved by means of several reactors connected one behind the other.

The present invention also provides hydrogenation catalysts which, besides palladium, vanadium and lead, contain in addition molybdenum, tungsten and/or rhenium on a ceramic support having a BET surface area of less than 40 $m^3/g$ and wherein the palladium content is from 1 to 50 g, the vanadium content is from 1 to 50 g, the lead content is from 1 to 20 g and the total content of molybdenum, tungsten and/or rhenium is from 1 to 20 g per liter of ceramic support material.

Suitable support materials are in particular the support materials described above, especially α-aluminium oxide.

The process according to the invention using the new catalysts is distinguished in particular by hitch space-time yields, combined with a diminution of the scale of the apparatus required and the significantly increased productivity of the catalysts. Consequently a considerable increase in production can be achieved in existing plants. Moreover the process according to the invention is distinguished by a particularly high selectivity with regard to the hydrogenation product.

EXAMPLES

Catalyst Preparation

Example 1 (Comparison Example)

One liter of an α-$Al_2O_3$ support in the form of spheres having a diameter of 3 to 5 millimeters, a BET surface area of 9.8 $m^2/g$, an absorption capacity of 45.1 ml water per 100 g of support and a bulk density of 812 g/l was impregnated with 366 ml of an aqueous solution containing 10.8 g NaOH (corresponding to 0.27 gram equivalents). The solution was completely absorbed by the support within a few minutes.

The moist support was dried in a warm, vigorous ascending current of air. The drying time required to achieve constant weight was about 15 minutes. The residual moisture content after cooling was approximately 1% of the absorption capacity of the support.

The dry support pretreated in this way was impregnated, appropriately to its absorption capacity, with 366 ml of an aqueous sodium tetrachloropalladate solution containing 9 g palladium (corresponding to 0.169 gram equivalents) and left to stand for 15 minutes. To reduce the palladium compound deposited on the support to metallic palladium, the catalyst was covered with 400 ml of a 10% aqueous solution of hydrazine hydrate and left to stand for 2 hours. The catalyst was then thoroughly rinsed with deionised water until the ions of the compounds used for the preparation of the catalyst were no longer detectable in the rinsing water; this was the case after about 10 hours.

Subsequently the product was again dried to constant weight in a vigorous, warm ascending current of air.

The Pd-containing catalyst was then impregnated with 366 ml of an aqueous solution containing 9 g vanadium in the form of vanadyl oxalate. The drying of the support in the warm current of air was carried out as specified above. The catalyst was then heat-treated in a tubular furnace for 6 hours at 300° C. in the course of which the oxalate was decomposed.

The catalyst was then impregnated with 366 ml of an aqueous solution containing 3 g of lead in the form of lead acetate and again dried in the ascending current of air.

The prepared catalyst contained 9 g palladium, 9 g vanadium and 3 g lead and corresponded to the catalyst of Example 1 in DE-OS 2 849 002.

Example 2

One liter of an $\alpha\text{-}Al_2O_3$ support in the form of spheres having a diameter of 3 to 5 millimeters, a BET surface area of 9.8 $m^2/g$, an absorption capacity of 45.1 ml water per 100 g of support and a bulk density of 831 g/l was impregnated with 367 ml of an aqueous solution containing 48 g NaOH (corresponding to 1.2 gram equivalents). The solution was completely absorbed by the support within a few minutes.

The moist support was dried in a warm vigorous ascending current of air. The driving time required to achieve constant weight was about 15 minutes. The residual moisture content after cooling was approximately 1% of the absorption capacity of the support.

The dry support pretreated in this way was impregnated, appropriately to its absorption capacity, with 352 ml of an aqueous sodium tetrachloropalladate solution containing 40 g palladium (corresponding to 0.751 gram equivalents) and left to stand for 24 hours. To reduce the palladium compound deposited on the support to metallic palladium, the catalyst was covered with 400 ml of a 10% aqueous solution of hydrazine hydrate and left to stand for 2 hours. The catalyst was then thoroughly rinsed with deionised water until the ions of the compounds used for the preparation of the catalyst were no longer detectable in the rinsing water; this was the case after about 10 hours.

Subsequently the product was again dried to constant weight in a vigorous, warm ascending current of air.

The Pd-containing catalyst was then impregnated with 365 ml of an aqueous solution containing 40 g vanadium in the form of vanadyl oxalate. The drying of the support in the warm current of air was carried out as specified above. The catalyst was then heat-treated in a tubular furnace for 4 hours at 300° C., in the course of which the oxalate was decomposed.

The catalyst was then impregnated with 365 ml of an aqueous solution containing 14 g of lead in the form of lead acetate and 14 g rhenium in the form of $Re_2O_7$ and again dried in the ascending current of air.

The prepared catalyst contained 40 g Pd, 40 g vanadium, 14 g lead and 14 g rhenium per liter of support. The catalyst was evenly mixed with one liter of untreated support material.

Examples of the Hydrogenation of Nitrobenzene

Example 3 (Comparison Example)

A bed (285 cm in height) of a catalyst prepared as in Example 1 was placed in a reactor tube having an internal diameter of approx. 26 mm, which was thermostatically controlled using oil. The catalyst was flushed first with nitrogen, then with hydrogen and was subsequently heated to 240° C. over 5 hours in a current of hydrogen of approx. 1.528 NL/h. Vaporisation of nitrobenzene in the current of hydrogen was then commenced. The nitrobenzene-hydrogen mixture reached the surface of the catalyst bed at a temperature of approx. 230° C. The specific loading of the catalyst was increased within 80 hours from 0.2 to 1.05 kg/l×h, which corresponds to a loadings per unit area of 2.994 $kg/m^2\times h$, so that on average a loading of 1.03 kg/l×h was attained. Throughout the process care was taken to ensure that at no point on the catalyst would the temperature exceed 440° C.

The oil temperature was increased from 240° C. to 300° C. in 20° C. steps after approx. 700, 800 and 900 hours. The change in the oil temperature along the reactor tube was approx. ±1° C. The flow rate of the oil along the surface of the tube was to approximately 1.5 m/s.

The catalyst achieved a useful life of approx. 1,050 hours, after which the nitrobenzene content of the condensate increased from 0 to approx. 300 ppm and as a result the catalyst had to be regenerated by burning off.

The average selectivity was 99.0%. After the regeneration, in the second cycle the performance of the catalyst was unchanged, with a useful life of 990 hours and 99.2% selectivity.

Example 4

A bed (285 cm in height) of a catalyst prepared and diluted as in Example 2 was placed in a reactor tube having an internal diameter of approx. 26 mm, which was thermostatically controlled using oil. The catalyst was flushed first with nitrogen, then with hydrogen and was subsequently heated to 240° C. over 5 hours in a current of hydrogen of approx. 1.528 NL/h. Vaporisation of nitrobenzene in the current of hydrogen was then commenced. The nitrobenzene-hydrogen mixture reached the surface of the catalyst bed at a temperature of approx. 230° C. The specific loading of the catalyst was increased within 50 hours from 0.2 to 1.07 kg/l×h, which corresponds to a loading per unit area of 3.051 $kg/m^2\times h$, so that on average a loading of 1.03 kg/l×h was attained. Throughout the process care was taken to ensure that at no point on the catalyst would the temperature exceed 440° C.

The oil temperature was increased from 240° C. to 300° C. in 10° C. steps after approx. 266, 270, 293, 314, 317 and 362 hours. The change in the oil temperature along the reactor tube was approx. ±1° C. The flow rate of the oil along the surface of the tube was approximately 1.5 m/s.

The catalyst achieved a useful life of approx. 394 hours, after which the nitrobenzene content of the condensate increased from 0 to approx. 300 ppm and as a result the catalyst had to be regenerated by burning off.

The average selectivity was 99.78%. After the regeneration, in the second cycle the catalyst showed a useful life of 876 hours and 99.7% selectivity; this was a marked increase in the useful life. The increase in the useful life continued in the third and fourth cycles, where it was 898 and 997 hours respectively.

The fourth cycle was operated in the first 220 hours using $N_2/H_2$ mixtures in order to improve the good starting selectivities still further (see Table 1).

TABLE 1

(Starting selectivities in the hydrogenation of nitrobenzene)

| Gas | $H_2/N_2$ | | $H_2$ | | $H_2$ | |
|---|---|---|---|---|---|---|
| Test | Example 4 | 4th run | Example 4 | 1st run | Example 3 | 1st run |
| Catalyst | Example 2 | | Example 2 | | Example 1 | |
| Average sel. | 99.7% | | 99.7% | | 99.0% | |
| Useful life | 997 h | | 394 h | | 1052 h | |
| Running time h | Loading kg/lxh | Select. % | Loading kg/lxh | Select. % | Loading kg/lxh | Select. % |
| 3.5 | 0.31 | 98.0 | 0.24 | 90.4 | 0.27 | 43.5 |
| 24 | 0.50 | 98.5 | 0.53 | 97.4 | 0.50 | 67.3 |
| 48 | 0.60 | 98.4 | 0.71 | 99.2 | 0.80 | 83.0 |
| 72 | 0.65 | 98.9 | 0.98 | 99.6 | 1.10 | 93.9 |
| 94 | 0.74 | 99.2 | 1.00 | 99.8 | 1.10 | 97.5 |

Examples of the Hydrogenation of o-Nitrotoluene

Example 5 (Comparison Example)

A bed (285 cm in height) of a catalyst prepared as in Example 1 was placed in a reactor tube having an internal diameter of approx. 33 mm, which was thermostatically controlled using oil. The catalyst was flushed first with nitrogen, then with hydrogen and was subsequently heated to 270° C. over 5 hours in a current of hydrogen of approx. 1.560 NL/h. Vaporisation of o-nitrotoluene in the current of hydrogen was then commenced. The o-nitrotoluene-hydrogen mixture reached the surface of the catalyst bed at a temperature of approx. 260° C. The specific loading of the catalyst was increased within 47 hours from 0.2 to 0.62 kg/lxh, which corresponds to a loading per unit area of 1,097 kg/m²xh, so that on average a loading of 0.58 kg/lxh was attained. Throughout the process care was taken to ensure that at no point on the catalyst would the temperature exceed 440° C.

The change in the oil temperature along the reactor tube was approx. ±1° C. The flow rate of the oil along the surface of the tube was approximately 1.5 m/s.

The catalyst achieved a useful life of approx. 216 hours, after which the o-nitrotoluene content of the condensate increased from 0 to approx. 300 ppm and as a result the catalyst had to be regenerated by burning off. Under the boundary conditions given the catalyst has therefore achieved a productivity of > approx. 125 kg/l.

The average selectivity was 99.85%.

After the regeneration, in the second cycle the performance of the catalyst was almost unchanged, with a useful life of 198 hours and 99.85% selectivity.

Example 6

A bed (285 cm in height) of a catalyst prepared as in Example 2 was placed in a reactor tube having an internal diameter of approx. 33 mm, which was thermostatically controlled using oil. The catalyst was flushed first with nitrogen, then with hydrogen and was subsequently heated to 270° C. over 5 hours in a current of hydrogen of approx. 1.560 NL/h. Vaporisation of o-nitrotoluene in the current of hydrogen was then commenced. The o-nitrotoluene-hydrogen mixture reached the surface of the catalyst bed at a temperature of approx. 260° C. The specific loading of the catalyst was increased within 50 hours from 0.13 to 0.689 kg/lxh, which corresponds to a loading per unit area of 1,219 kg/m²xh, so that on average a loading of 0.644 kg/lxh was attained. Throughout the process care was taken to ensure that at no point on the catalyst would the temperature exceed 440° C.

The change in the oil temperature along the reactor tube was approx. ±1° C. The flow rate of the oil along the surface of the tube was approximately 1.5 m/s. The catalyst achieved a useful life of approx. 239 hours, after which the o-nitrotoluene content of the condensate increased from 0 to approx. 300 ppm and as a result the catalyst had to be regenerated by burning off. Under the boundary conditions given the catalyst therefore has achieved a productivity of > approx. 154 kg/l.

The average selectivity was 99.82%.

After the regeneration, in the second cycle the catalyst showed a useful life of 439 hours and 99.87% selectivity; this was a marked increase in the useful life. After the eleventh regeneration, in the twelfth cycle the catalyst achieved a useful life of 525 hours and an average selectivity of 99.9%.

Within the period investigated, the catalyst according to the invention therefore has a satisfactory useful life accompanied by high loading over many regenerations.

What is claimed is:

1. A process for the production of an aromatic amine comprising hydrogenating a nitroaromatic compound in the gas phase at a temperature of from about 180 to about 500° C. in the presence of a catalyst bed comprising a catalyst on a ceramic support having a BET surface area of less than 40 m³/g comprising a) palladium,
   b) vanadium,
   c) lead, and
   d) at least one metal or compound containing a metal selected from the group consisting of molybdenum, tungsten, rhenium and combinations thereof, in amounts such that a molar ratio of hydrogen to nitro groups of from 3:1 to 30:1 is present.

2. A hydrogenation catalyst on a ceramic support material having a BET surface area of less than 40 m³/g comprising a) from 1 to 50 grams of palladium,
   b) from 1 to 50 grams of vanadium, and
   c) from 1 to 20 grams of lead, and
   d) a total of from 1 to 20 grams of a metal or metal-containing compound containing molybdenum, tungsten and/or rhenium for each liter of ceramic support material.

* * * * *